United States Patent
Lee et al.

(10) Patent No.: US 8,004,677 B2
(45) Date of Patent: Aug. 23, 2011

(54) FOCUSED-BEAM ELLIPSOMETER

(75) Inventors: Joong Whan Lee, Daejeon (KR); Young June Ko, Daejeon (KR); Young Sun Park, Chungcheongnam-do (KR); Yoon Jong Park, Gyeonggi-do (KR); Chi Woon Jeong, Seoul (KR); Sang Heon Ye, Busan (KR); Yong Jai Cho, Daejeon (KR); Hyun Mo Cho, Daejeon (KR); Won Chegal, Daejeon (KR)

(73) Assignees: Korea Research Institute of Standards and Science, Daejeon (KR); K-MAC, Daejeon (KR)

( * ) Notice: Subject to any disclaimer, the term of this patent is extended or adjusted under 35 U.S.C. 154(b) by 298 days.

(21) Appl. No.: 12/308,662

(22) PCT Filed: Jun. 20, 2007

(86) PCT No.: PCT/KR2007/002992
§ 371 (c)(1), (2), (4) Date: Dec. 19, 2008

(87) PCT Pub. No.: WO2007/148918
PCT Pub. Date: Dec. 27, 2007

(65) Prior Publication Data
US 2010/0045985 A1   Feb. 25, 2010

(30) Foreign Application Priority Data
Jun. 22, 2006 (KR) .......... 10-2006-0056275

(51) Int. Cl.
*G01J 4/00* (2006.01)
(52) U.S. Cl. ........................... 356/369
(58) Field of Classification Search ............. None
See application file for complete search history.

(56) References Cited

U.S. PATENT DOCUMENTS

| | | | |
|---|---|---|---|
| 4,999,014 A | 3/1991 | Gold et al. | |
| 5,042,951 A | 8/1991 | Gold et al. | |
| 5,181,080 A | 1/1993 | Fanton et al. | |
| 6,798,511 B1 | 9/2004 | Zhan et al. | |
| 6,831,743 B2 * | 12/2004 | Aspnes et al. | 356/369 |
| 7,385,699 B2 * | 6/2008 | Mieher et al. | 356/401 |
| 2004/0233439 A1 * | 11/2004 | Mieher et al. | 356/401 |

FOREIGN PATENT DOCUMENTS
EP 0 396 409 11/1990
JP 2005-98923 4/2005

OTHER PUBLICATIONS

Masetti et al., In Situ Monitoring of film deposition with an ellipsometer based on a four detector photopolarimeter, Oct. 1996, Applied Optics, vol. 35, No. 28, pp. 5626-5629.*

* cited by examiner

*Primary Examiner* — Gregory J Toatley
*Assistant Examiner* — Juan D Valentin
(74) *Attorney, Agent, or Firm* — Clark & Brody

(57) ABSTRACT

The present invention relates to an ellipsometer, and more particularly, to an ellipsometer to find out the optical properties of the sample by analyzing the variation of the polarization of a light which has specific polarisation then reflected on a surface of the sample.

4 Claims, 5 Drawing Sheets

FOCUSED-BEAM ELLIPSOMETER

TECHNICAL FIELD

The present invention relates to a focused-beam ellipsometer, and more particularly, to an ellipsometer for analyzing polarization, which light having specific polarization has before the light is incident to and then reflected on a surface of a sample, to find optical properties of the sample.

BACKGROUND ART

In most studies for physics, chemistry and material fields, it is very important to measure optical properties of materials and a thickness of a thin film. Particularly, in recent semiconductor and display industries, it is very important to define and control thicknesses and optical properties of PR, ITO, and gate oxide films between fabricating processes in an aspect of an yield of product and improvement of performance.

Various principles have currently been known to measure optical properties of materials and a thickness of a thin film. Among them, an ellipsometry is much improved in its performance with development of a light source, an optical detector and a computer and is largely increased in its application with increasing of processes using thin films and surfaces.

The ellipsometry is divided into a reflection type and a transmission type and the reflection type ellipsometry, which analyzes a polarization of light reflected from a surface of a sample with an incidence angle, is widely used. The reflection type ellipsometry may mainly be used for obtaining optical properties of the sample such as a refractive index and an extinction coefficient by measuring variation in polarization of light reflected by the sample and may also be used for obtaining properties such as surface state of the sample.

A plane which is perpendicular to a surface of the sample and is on a light path is defined as an incidence surface. A case that direction of an electric field vector of light is perpendicular to the incidence surface is referred to s-wave and a case that direction of the electric field vector of the light is on the incidence surface is referred to p-wave.

If a structure of a sample and optical properties, a thickness of a thin film and an incidence angle of element materials of the sample are given, reflection coefficients of the s-wave and the p-wave respectively $r_s$ and $r_p$ in a specific wavelength are calculated by the following equations.

$$r_p = \frac{E_{rp}}{E_{ip}} = |r_p| e^{i\delta_p}$$

$$r_s = \frac{E_{rs}}{E_{is}} = |r_s| e^{i\delta_s}$$

wherein, $|r_{p(s)}|$ is a ratio of an electric field $E_{rp(s)}$ of an reflected wave to an electric field $E_{ip(s)}$ of an incident wave. In addition, $\delta_{p(s)}$ is a phase variation due to a reflection. In the ellipsometry, a complex reflection coefficient ratio $\rho$, which is a reflection coefficient ratio of the p-wave to the s-wave, is defined as follows:

$$\rho = \frac{r_p}{r_s} = \left|\frac{r_p}{r_s}\right| e^{i(\delta_p - \delta_s)}$$

From this, ellipsometric angles $\psi$ and $\Delta$ are defined as follows:

$$\psi = \tan^{-1}\left(\left|\frac{r_p}{r_s}\right|\right)$$

$$\Delta = \delta_p - \delta_s$$

wherein, $\tan \psi$ is a magnitude ratio of reflection coefficient and $\Delta$ is a phase difference between the p-wave and the s-wave after the p-wave and the s-wave incident with the same phase are reflected Ellipsometers having various functions and structures are disclosed in prior patents and papers. As a typical ellipsometer, there are a null ellipsometer which finds a null point by controlling a linear polarizer and a compensator, a rotating-polarizer ellipsometer in which a linear polarizer of a light source part module rotates at a constant speed, a rotating-analyzer ellipsometer in which a linear polarizer of a light receiving part module rotates at a constant speed or a rotating-compensator ellipsometer in which a compensator of a light receiving part module rotates at a constant speed.

Figure 1:
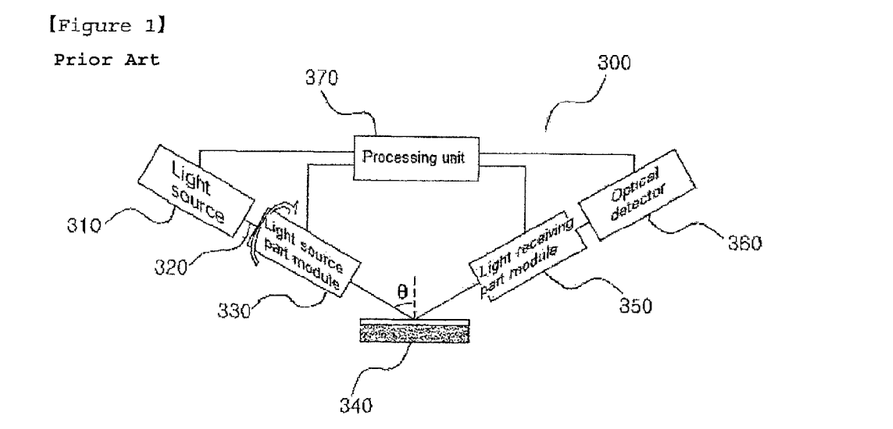
FIG. 1 is a block diagram illustrating a conventional rotating-compensator ellipsometer.

FIG. 1 shows a rotating-polarizer ellipsometer which is one of the widely used ellipsometers. The rotating-polarizer ellipsometer 300 is provided with a light source part module 330, in which a linear polarizer rotates at a constant speed by a step motor or a DC motor, so as to polarize light 320 emitted from a light source 310. The light source part module 330 may consist of a collimating lens, a linear polarizer and so on. The light passed through the light source part module 330 is linearly polarized and the polarization axis rotates at the same speed as the driving motor. The light reflected on a surface of a sample is received by a light receiving part module 350 after its polarization is varied due to optical properties of the sample. The light receiving part module 350 may consist of a linear polarizer, a compensator and so on and allows a filtered specific polarization component to transmit. An optical detector 360 detects an intensity of the light passed through the light receiving part module 350 and incident thereto as an electric signal such as voltage or current. The intensity signal of the detected light is processed in a processing device 370 in combination with information of an azimuth angle of polarization axis of the polarizer in the light source part module 330 and information of an azimuth angle of polarization axis of the polarizer in light receiving part module 350.

In the above mentioned ellipsometer, as the light source, a white light source such as a tungsten halogen lamp, a xenon lamp, etc. and a monochromatic light source such as a laser, etc. may be used. The light source part module 330 or the light receiving part module 350 may be added with a spectroscope when a white light source is used. Besides the above mentioned ellipsometer, various ellipsometers have been developed and varied structures may be obtained from the basic structure through adding, removing or driving a compensator, a phase modulation device, etc.

In the case of a rotating-polarizer ellipsometer in FIG. 1, the light source part module 320 and the light receiving part 350 consist of a linear polarizer alone, respectively and the azimuth angle of polarization axis of the polarizer of the light source part module 330 rotates at a uniform angular speed $\omega$, a voltage signal V(t) detected by the optical detector is a function of time t and may be expressed by the following equation.

$$V(t) = V_{av} + a \cos(2\omega t) + b \sin(2\omega t)$$

wherein, $V_{av}$ is a time average value of a voltage and a and b are Fourier coefficients for an angular frequency of $2\omega$. Fourier coefficients normalized by dividing both members of the equation by $V_{av}$ are as follows:

$$\alpha = \frac{a}{V_{av}} = \frac{\tan^2(\psi) - \tan^2(A)}{\tan^2(\psi) + \tan^2(A)}$$

$$\beta = \frac{b}{V_{av}} = \frac{2\tan(\psi)\cos(\Delta)\tan(A)}{\tan^2(\psi) + \tan^2(A)}$$

wherein, A is the azimuth angle of polarization axis of the polarizer in the light receiving part module 350. Putting in order again the equation, the ellipsometric angle is obtained using the following relation equation.

$$\psi = \tan^{-1}\left(\sqrt{\frac{1+\alpha}{1-\alpha}\tan A}\right)$$

$$\Delta = \cos^{-1}\left(\frac{\beta}{\sqrt{1-\alpha^2}}\right)$$

The resultant ellipsometric angles $\psi$ and $\Delta$ derived from the above can be expressed with Fresnel reflection coefficients $r_p$ and $r_s$ for p polarized light and s polarized light and thus physical quantities of a sample can be obtained in a process of comparing them with values of $\psi$ and $\Delta$ calculated using model equations suitable to optical properties of the sample 340.

The ellipsometry is a technology belonging to an optical metrology among methods for measuring optical properties of a material and a thickness of a thin film and has a superiority of being sensitive to an ultra thin film compared to similar technologies such as reflectometry, interferometry, etc.

Since a rotating-analyzer ellipsometer, a rotating-polarizer ellipsometer and a rotating-compensator ellipsometer which are generally and widely used have, due to its structure, a driving part which rotates mechanically by a step motor or a DC motor, a measuring time is limited according to a speed of the motor and signal noise due to vibration generated from mechanical rotation exists always.

In a phase modulation type which is another type of an ellipsometer, the measuring time is limited by a phase modulation frequency of a photoelastic modulator. The rotation speed of the polarizer is about 10~100 Hz in the rotating-polarizer ellipsometer and the phase modulation frequency is about 50 kHz in the phase modulation type ellipsometer and thus the phase modulation type ellipsometer is relatively suitable to a high speed measurement, but a thermostat is required since the photoelastic modulator has a temperature dependency and a light wavelength dependency and there is a difficulty of correcting optical properties of the photoelastic modulator for wavelengths of used light.

Structures similar to a structure of the focused-beam ellipsometer according to the present invention are disclosed in U.S. Pat. Nos. 4,999,014, 5,042,951 and 5,181,080. Such prior patents have intended to improve an accuracy of a measurement result for a nano thin film. However, in the focused-beam ellipsometry of the prior patent, there has necessarily been a limitation in improvement of measurement accuracy for $\psi$ and $\Delta$ since $\psi$ and $\Delta$ are calculated by taking a part of reflected light formed by a structure of the focused-beam ellipsometer.

DISCLOSURE

Technical Problem

An object of the present invention is to provide a novel principle of an ellipsometer, which is improved from the conventional rotating-analyzer ellipsometer and rotating-polarizer ellipsometer requiring a constant speed rotation driving part by a motor to be capable of measuring without the constant speed rotation driving part and thus it is possible to measure more accurately and in high speed an ellipsometric angle by taking polarization components for multiple incidence surfaces of 360° in a static state is possible.

Technical Solution

The ellipsometer in accordance to the present invention includes
a light source; a light source part module provided with a linear polarizer for polarizing light emitted from the light source; a beam splitter for splitting the light polarized by the light source part module; an objective lens for permitting some part of the light split by the beam splitter to pass through and to be convergently irradiated to a sample; a light receiving part module provided with an analyzer which is a polarizer for filtering specific polarization of the light reflected on the sample and receiving the light which is reflected on the sample and passed through the objective lens and the beam splitter; an optical detector for detecting the light received to the light receiving part module with unit devices; and a processing device for correcting an intensity of the light detected by the optical detector to a value corresponding to unit devices of the optical detector along a passage of multiple incidence surfaces of 360° and processing the value.

In addition, the optical detector may be a charge coupled device which has a plurality of unit devices and thus is capable of measuring a two-dimensional image.

Further, each of the light source part module and the light receiving part module may further include a filter for permitting light in a range of specific wavelength to pass through.

Furthermore, each of the light source part module and the light receiving part module may further include a collimating lens and a compensator.

DESCRIPTION OF DRAWINGS

The above and other objects, features and advantages of the present invention will become apparent from the following description of preferred embodiments given in conjunction with the accompanying drawings, in which.

DETAILED DESCRIPTION OF MAIN ELEMENTS

110: light source
120: light source part module

130: beam splitter
140: objective lens
150: sample
160: light receiving part module
170: optical detector
171: unit device
180: processing device

BEST MODE

Hereinafter, the embodiments of the present invention will be described in detail with reference to accompanying drawings.

Figure 2:
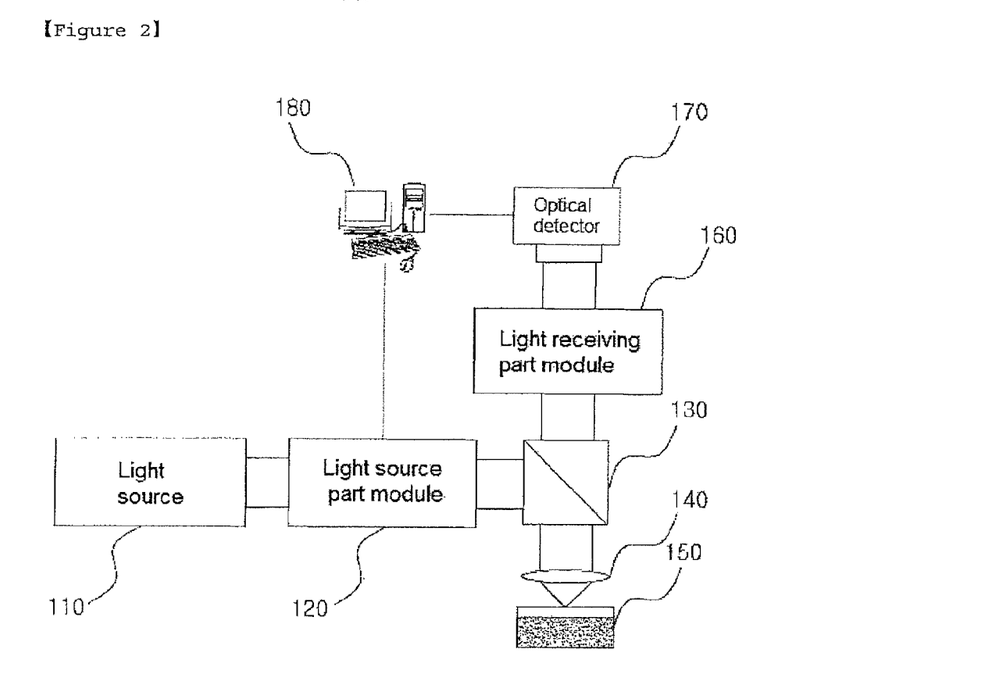
FIG. 2 is a block diagram illustrating a focused-beam ellipsometer according to the present invention.
Figure 3:
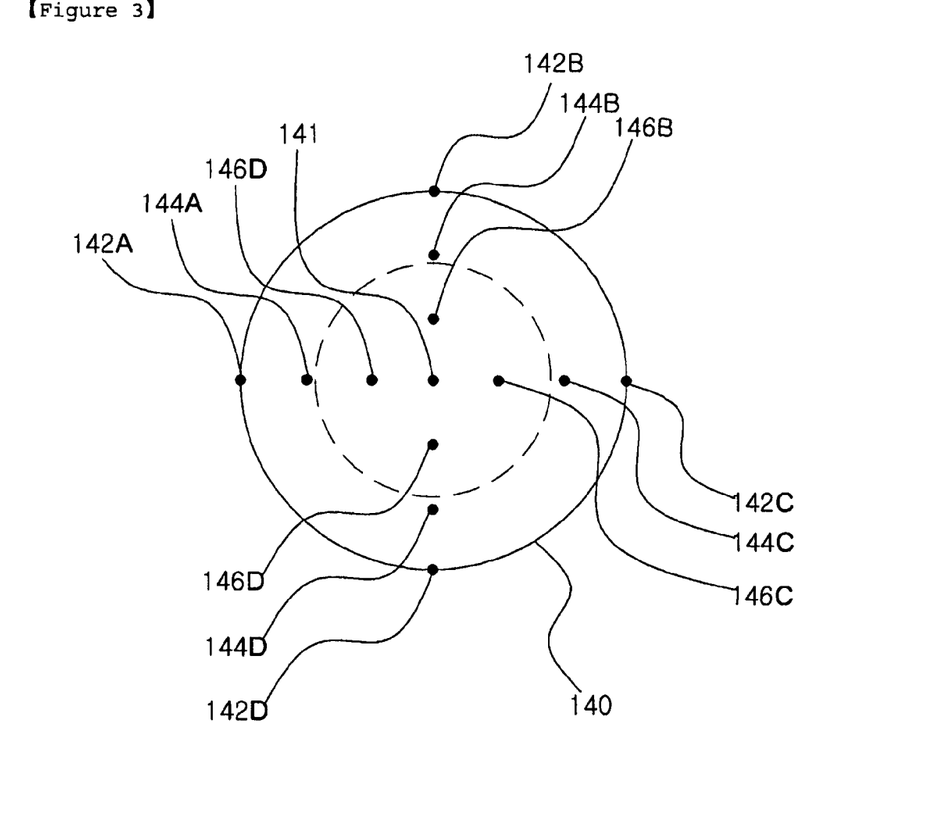
FIG. 3 is a view showing light incident to a sample by an objective lens according to image position detected by an optical detector.
Figure 4:
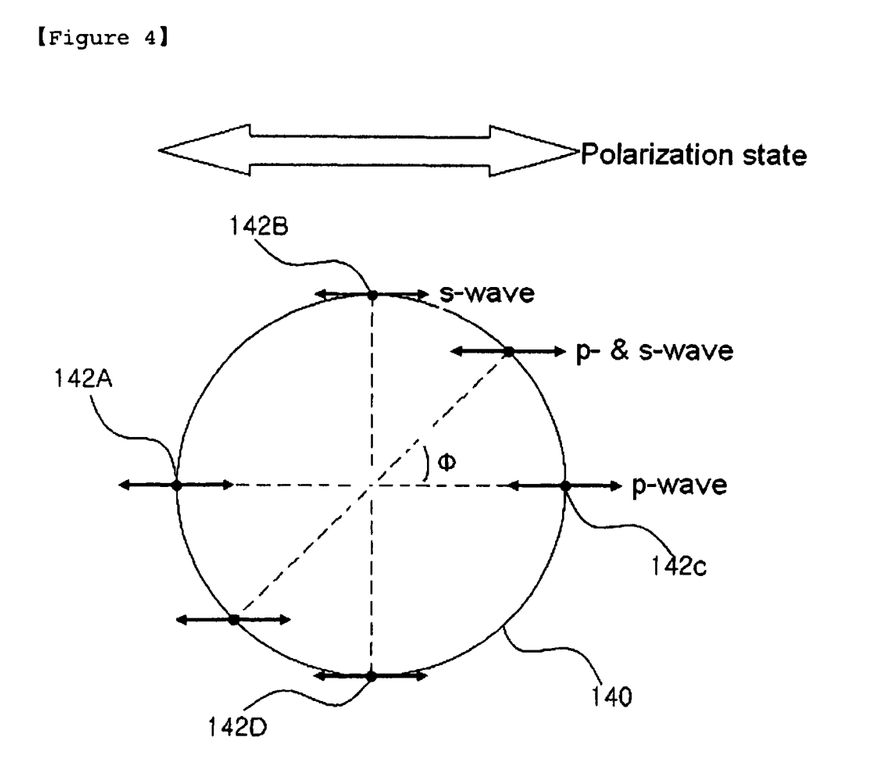
FIG. 4 is a view illustrating polarization state according to position of light incident to the sample by the objective lens.
Figure 5:
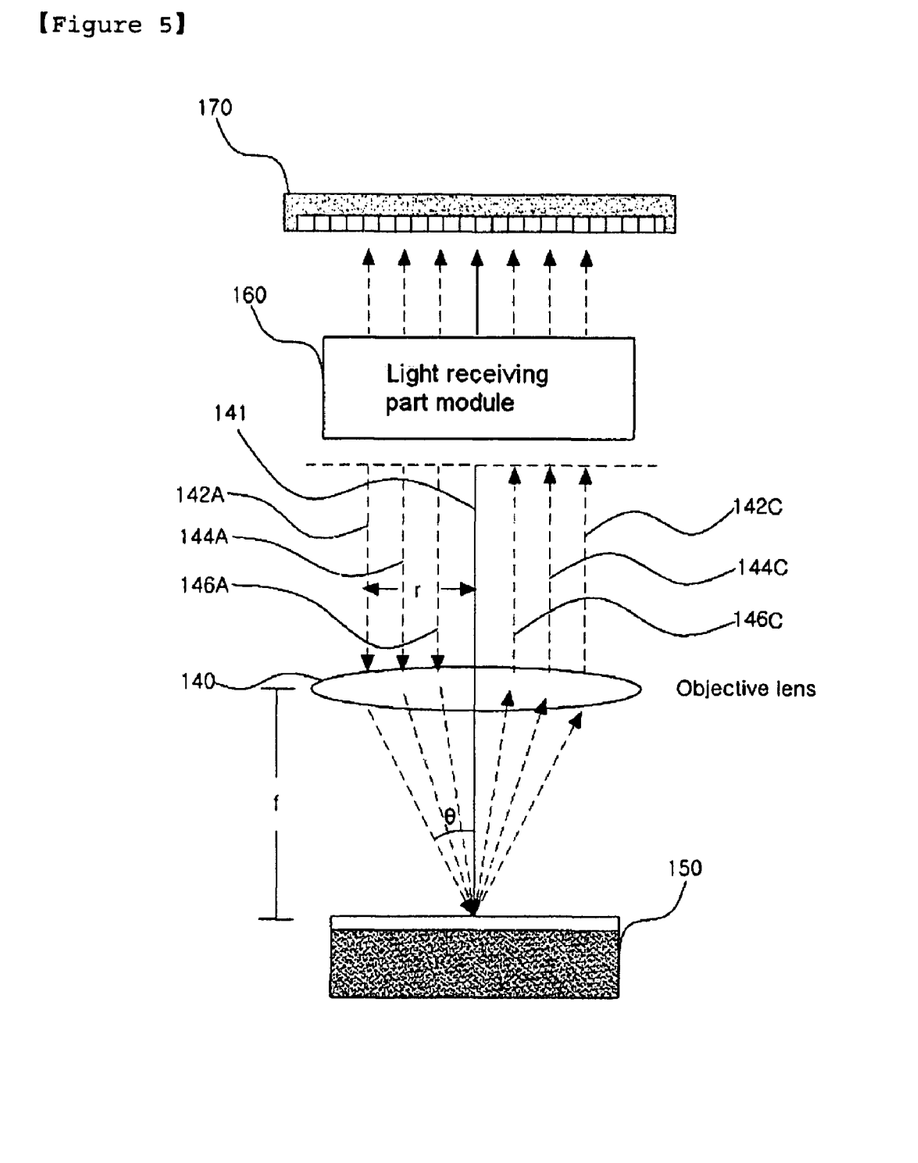
FIG. 5 is a view illustrating a state that light is incident to and reflected on a surface of the sample.
Figure 6:
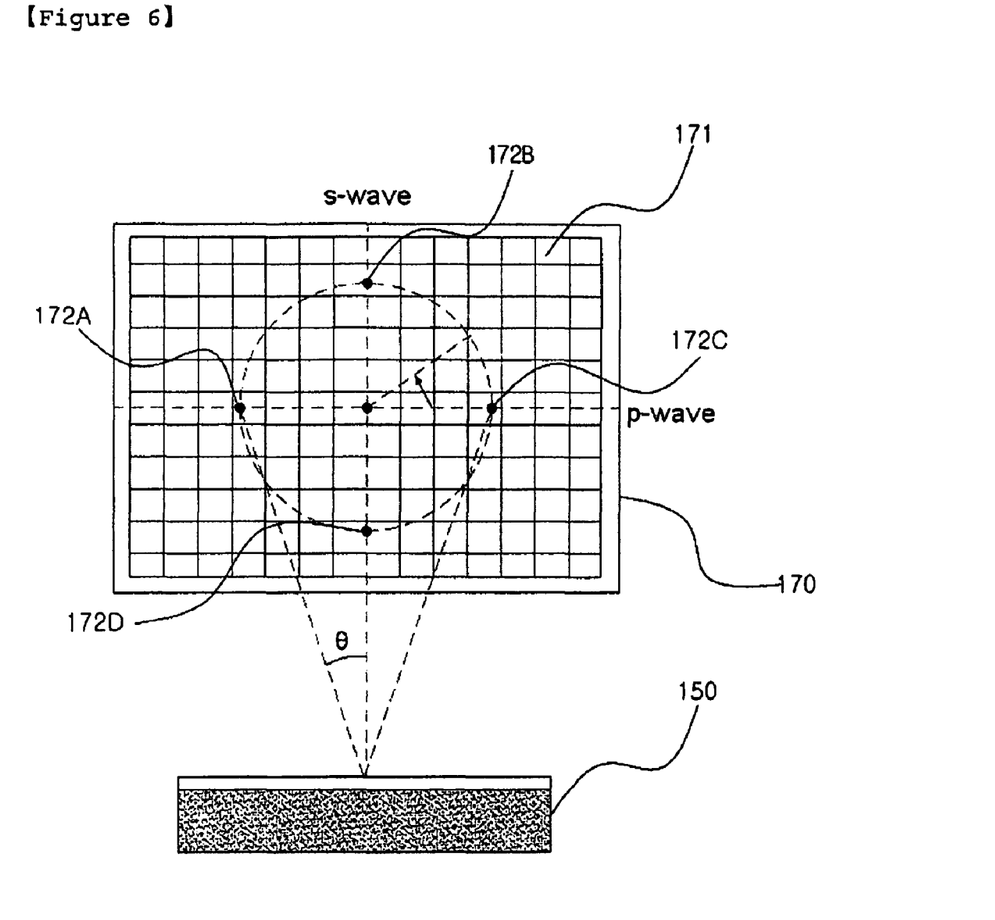
FIG. 6 is a view illustrating a state that light reflected on the surface of the sample is incident to a unit device of the optical detector.

FIG. 2 is a block diagram illustrating a focused-beam ellipsometer according to the present invention; FIG. 3 is a view in which light incident to a sample by an objective lens is shown according to image position detected by an optical detector; FIG. 4 is a view illustrating polarization state according to position of light incident to the sample by the objective lens; FIG. 5 is a view illustrating a state that light is incident to and reflected on a surface of the sample; and FIG. 6 is a view illustrating a state that light reflected on the surface of the sample is incident to a unit device of the optical detector.

As shown, an ellipsometer according to the present invention for performing a measurement for a thickness of a thin film and optical properties of a sample includes a light source 110; a light source part module 120 provided with a linear polarizer for linear polarizing light emitted from the light source 110; a beam splitter 130 for splitting the light polarized by the light source part module 120; an objective lens 140 for convergently irradiating some part of the light split by the beam splitter 130 to a sample; a light receiving part module 160 for receiving the light reflected on the sample; an optical detector 170 for detecting the light received to the light receiving part module 160 with unit devices; and a processing device 180 for correcting and processing an intensity of the light detected by the optical detector 170.

The light source 110 may include a white light source such as a tungsten halogen lamp, a xenon discharge lamp, etc. and a monochromatic light source such as a laser, etc. and a specific laser may emit polarized light from itself. However, in the present invention, in order to define clearly a polarization direction of the light emitted from the light source 110, the light source part module 120 arranges the polarization direction of the light to a predetermined direction. The light emitted from the light source 110 is incident to the light source part module 120.

The light source part module 120 is provided with the linear polarizer for linear polarizing light emitted from the light source 110. The light emitted from the light source 110 passes through the light source part module 120 consisting of a linear polarizer and a compensator, etc. The light passed through the light source part module 120 comes to have a predetermined polarization direction according to arranged position of an optical device constructing the light source part module 120.

The beam splitter 130 serves to split the light polarized at the light source part module 120. A part of the split light passes the objective lens 140 disposed at a lower portion of the beam splitter 130 and the other part of the light is incident to the light receiving part module 160 disposed at up upper portion of the beam splitter 130. The other light split by the beam splitter 130 is incident to the light receiving part module 160 and is used to confirm a stability of the light source during the measurement.

The light passed through the beam splitter 130 is incident to the sample in a direction perpendicular to the sample and adjusted by the objective lens 140 having a large numerical aperture as shown in FIG. 2 so as to be focused to a surface of the sample. The objective lens 140 is disposed at the lower portion of the beam splitter 130 and serves to irradiate convergently the some part of the light split by the beam splitter 130 and passed therethrough to the sample.

The light reflected on the surface of the sample 150 passes through the objective lens 140 and the beam splitter 130 to be transferred to the light receiving part module 160.

In the drawing, the objective lens 140 and the sample 150 may be linearly disposed behind the beam splitter 130.

The light receiving part module 160 is disposed at the upper portion of the beam splitter 130, is provided with a linear polarizer for filtering specific polarization of the light reflected on the sample 150 and receives the light passing through the objective lens 140 and the beam splitter 130. Herein, the light receiving part module 160 serves to collimate the light so that a direction of the passed light is perpendicular to the optical detector 170 and to filter specific polarization component. The light receiving part module 160 may consist of a collimating lens, a pinhole, etc. like the light source part module 120 and, according to cases, may consist of a linear polarizer, a compensator, etc. as same as the light source part module 120. The light passed through the light receiving part module 160 is transferred to the optical detector 170.

The optical detector 170 detects the light received to the light receiving part module 160 with unit device and information obtained in each position of the optical detector 170 is transferred to the processing device 180 to be processed.

The processing device 180 corrects the intensity of the light detected by the optical detector 170 to a value corresponding to each unit device of the optical detector 170 [for example, the unit device is a pixel in a case that the optical detector is a charge coupled device (CCD)] along a passage of multiple incidence surfaces of 360° and processes the value. The optical detector 170 may include CCD which has many unit devices and is capable of measuring a two-dimensional image.

Hereinafter, a mechanism of the present invention for realizing the principle of the above described focused-beam ellipsometer will be described in detail.

FIG. 3 is a view showing light incident to a sample by an objective lens according to image position detected by an optical detector. The light incident to 142A is reflected on the surface of the sample 150 and passes through a position 142C which is in symmetry to a center 141 of the objective lens 140. Identically, the light incident to 142C passes through 142A after reflected on the surface of the sample 150. Referring to FIG. 5, the light incident to every positions of the objective lens 140 passes through a position which is in symmetry to a center 141 of the objective lens 140 and, at this time, lights incident to positions on a circumference having a radius of r on the objective lens 140 have the same incidence angle θ.

Since the light emitted from the light source in FIG. 2 comes to have a predetermined polarization direction while passing through the light source part module 120, the polarization direction according to a position of the light incident to the objective lens is expressed as shown in FIG. 4.

FIG. 4 is a view illustrating polarization direction according to positions of the light incident to the objective lens 140. Because, in the light, definition of the polarization direction is based on an incidence surface to which the light proceeds, polarization directions in positions on the same axis on the objective lens 140 are all the same and polarization directions on the same circumference are all different. The lights incident to 142A and 142C are p polarized and reflected on the sample and then pass through 142C and 142A respectively to go towards the optical detector. The lights incident to 142B and 142D are s polarized and reflected on the sample and then pass through 142D and 142B respectively to go towards the optical detector. Therefore, the light incident to an area of the objective lens 140 disposed between a line running from 142A to 142C and a line running from 142B to 142D has a polarization direction having both S-wave and P-wave components. The polarization direction is the same as the direction in which an axis is laid when rotating by φ from the position of the p polarization. At this time, the polarization component on the objective lens 140 is a value which is determined by a polarization component of the light which is incident to the objective lens 140.

FIG. 5 illustrates the objective lens 140 and a step in which the light passed through the objective lens 140 is focused on the surface of the sample 150. the beam incident to the objective lens 140 is refracted by a numerical aperture of the objective lens 140 to be incident to the surface of the sample 150 and an incidence angle θ of the beam incident to the surface of the sample 150 is determined by the numerical aperture of the objective lens 140. If an angle between the beam passing through the center of the objective lens 140 and the beam passing through the most outer periphery of the objective lens 140 is $\theta_{max}$, $\theta_{max}$ is expressed by the following equation with the numerical aperture of the objective lens 140.

$$\theta_{max} = \sin^{-1}(N.A.)$$

More specifically, the light 142A incident to the most outer periphery is reflected on the surface of the sample 150 and passes through the position 142C which is in symmetry to the center 141 of the objective lens 140 and then is incident to the optical detector 170. Likely, the lights 144A and 146A incident to the next positions are reflected on the surface of the sample 150 and pass through the positions 144C and 146C which are in symmetry to the center of the objective lens 140 and then are incident to the optical detector 170. On the contrary, the beam incident to the center of the objective lens 140 is reflected on the surface of the sample 150 and passes again through the center of the objective lens 140 to be incident to the optical detector 170. In other words, the lights between the center and the most outer periphery of the objective lens 140 are reflected on the surface of the sample 150 and pass through the positions which are in symmetry to the center of the objective lens 140 and then are incident to the optical detector 170.

At this time, when reflected on the surface of the sample 150, the incidence angle is defined by an inside angle between the center 141 of the objective lens 140 and a passage through which the incident light passes. With obtaining a signal of the light incident to the optical detector 170 according to a position of the unit device of the optical detector 170, variation in the light reflected on the surface of the sample 150 at various incidence angles is obtained. Only several beams are illustrative in FIG. 3 and FIG. 5 but, since the beam exist actually in countless numbers, resolution of the incidence angle is determined by a size and distance of the unit device of the optical detector 170.

FIG. 6 illustrates the light which is reflected on the surface of the sample 150, passes through the objective lens 140 and is incident to the optical detector 170. At this time, since a surface of the optical detector 170 consists of many unit devices 171, it is possible, as shown in FIG. 5, to analyze an image formed on the optical detector 170 to the unit device 171 of the optical detector 170 by matching one direction in which the unit devices 171 are arranged to the polarization component of the light incident to the sample 150. Referring to FIG. 4, the light, which is incident to 142A and is reflected on the surface of the sample 150 and then goes out through 142C, forms an image at 172C of FIG. 6. Identically referring to FIG. 4 and FIG. 5, the light, which is incident to 142C and goes out through 142A and then is transferred to the optical detector 170, forms the image at 172A; the light, which is incident to 142B and goes out through 142D, forms the image at 172D of the optical detector 170; and the light, which is incident to 142D and goes out through 142B, forms the image at 172B of the optical detector 170.

Therefore, like in the objective lens, the P-wave component and the S-wave component coexist between the P-wave direction and the S-wave direction and it is possible to obtain measured value according to variation in polarization direction of the light which is incident to the surface of the sample by obtaining values measured at the unit devices on the same circumference having a radius of r from an axis which is matched to the polarization direction of the light incident to the surface of the sample. With such manner, it is possible to obtain a result similar to that in the rotating-analyzer ellipsometer or the rotating-polarizer ellipsometer by obtaining component having the same incidence angle on the basis of the center axis 141 of the objective lens 140.

INDUSTRIAL APPLICABILITY

The focused-beam ellipsometer according to the present invention, because it is possible to measure the ellipsometric coefficient without a constant speed driving part by a step motor or a DC motor compared with the conventional rotating-analyzer, rotating-polarizer and rotating-compensator ellipsometers which are currently widely used, has advantages that a measurement accuracy is relatively improved and the measurement speed is improved to a driving speed of the optical detector as it is possible to eliminate signal noise due to vibration of the motor and an error due to rotation of the optical part. In addition, it is possible to measure more accurately the ellipsometric coefficient by taking polarization components for multiple incidence surfaces of 360° in a static state compared with the conventional focused-beam ellipsometer which takes a polarization component for a single incidence surface.

The invention claimed is:

1. An ellipsometer, comprising:
   a light source;
   a light source part module provided with a polarizer for polarizing light emitted from the light source;
      a beam splitter for splitting the light polarized by the light source part module; an objective lens for permitting some part of the light split by the beam splitter to pass through and to be convergently irradiated to a sample;
      a light receiving part module provided with a polarizer for elliptic polarizing the light reflected on the sample and receiving the light which is reflected on the sample and passed through the objective lens and the beam splitter;
      an optical detector for detecting the light received to the light receiving part module with a plurality of pixels; and
      a processing device for
      obtaining light intensities for multiple incidence surfaces of 360° measured in a static state by the pixels, each of which has a different azimuth angle, on a same circumference having a radius of r and calculating ellipsometric angles (ψ, Δ) from the light intensities.

2. The ellipsometer as set forth in claim 1, wherein the optical detector is a two-dimensional image measuring apparatus.

3. The ellipsometer as set forth in claim 1, wherein each of the light source part module and the light receiving part module further includes a filter for permitting light in a range of specific wavelength to pass through.

4. The ellipsometer as set forth in claim 3, wherein each of the light source part module and the light receiving part module further includes a collimating lens and a compensator.

* * * * *